| (12) | United States Patent | (10) Patent No.: | US 9,538,914 B2 |
|---|---|---|---|
| | Hauger et al. | (45) Date of Patent: | Jan. 10, 2017 |

(54) MICROSCOPY SYSTEM FOR OBSERVING FLUORESCENCE IN OPHTHALMOLOGY

(71) Applicant: Carl Zeiss Meditec AG, Jena (DE)

(72) Inventors: Christoph Hauger, Aalen (DE); Holger Matz, Unterschneidheim (DE); Anja Seiwert, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 178 days.

(21) Appl. No.: 14/299,488

(22) Filed: Jun. 9, 2014

(65) Prior Publication Data

US 2014/0362343 A1 Dec. 11, 2014

(30) Foreign Application Priority Data

Jun. 11, 2013 (DE) .................. 10 2013 009 817

(51) Int. Cl.

| A61B 3/14 | (2006.01) |
|---|---|
| A61B 3/13 | (2006.01) |
| A61B 3/00 | (2006.01) |
| G02B 21/00 | (2006.01) |
| G02B 21/16 | (2006.01) |
| G02B 21/22 | (2006.01) |

(52) U.S. Cl.

CPC .............. *A61B 3/13* (2013.01); *A61B 3/0008* (2013.01); *G02B 21/0012* (2013.01); *G02B 21/16* (2013.01); *G02B 21/22* (2013.01)

(58) Field of Classification Search

USPC ....................................................... 351/206

See application file for complete search history.

(56) References Cited

U.S. PATENT DOCUMENTS

| 2001/0003490 A1 | 6/2001 | Kawasaki et al. |
|---|---|---|
| 2004/0109231 A1 | 6/2004 | Haisch et al. |
| 2008/0049314 A1 | 2/2008 | Steffen et al. |
| (Continued) | | |

FOREIGN PATENT DOCUMENTS

| DE | 266 024 A1 | 3/1989 |
|---|---|---|
| DE | 100 59 184 A1 | 8/2001 |
| (Continued) | | |

OTHER PUBLICATIONS

Horn; "3. Come and See Meeting"; Jul. 2011; pp. 1-12.

(Continued)

*Primary Examiner* — Jack Dinh (74) *Attorney, Agent, or Firm* — Patent Portfolio Builders PLLC (57) ABSTRACT

An ophthalmology microscopy system for observing fluorescence comprises an imaging system and an illumination system. The imaging system provides at least one optical imaging path producing a magnified multi-dimensional image of an object disposable in a focal plane of the imaging system, and comprises at least one optical observation filter. The illumination system provides an illumination beam path intersecting the focal plane of the imaging system at a variable angle of less than 90°. The microscopy system comprises first and second operating states. In the first operating state, radiation passing through the illumination beam path has at least in a section along the illumination beam path a spectrum free of a pass band of the observation filter. In the second operating state, radiation passing through the illumination beam path has a spectrum having a bandwidth of at least 200 nm in a range from 380 nm to 780 nm.

18 Claims, 2 Drawing Sheets

(56) References Cited

U.S. PATENT DOCUMENTS

| | | |
|---|---|---|
| 2008/0206149 A1 | 8/2008 | Haritoglou et al. |
| 2009/0059359 A1 | 3/2009 | Nahm et al. |
| 2009/0323181 A1 | 12/2009 | Andrews et al. |

FOREIGN PATENT DOCUMENTS

| | | |
|---|---|---|
| DE | 103 39 784 A1 | 3/2004 |
| DE | 10 2006 047 723 A1 | 2/2008 |
| DE | 10 2007 026 044 B3 | 8/2008 |
| DE | 10 2007 041 439 A1 | 3/2009 |
| WO | 2006/133903 A2 | 12/2006 |

OTHER PUBLICATIONS

Wikipdeia; "Gilosis"; [downloaded from Internet at http://en.wikipedia.org/wiki/Gilosis]; Aug. 7, 2014; pp. 1-8.

Wikipedia; "Epiretinal membrane"; [downloaded from Internet at http://en.wikipedia.org/wiki/Epiretinal_membrane]; Aug. 7, 2014; pp. 1-4.

Mayofrides, E.; "Indocyanine green-assisted internal limiting membrane peeling for macular holes: toxicity?"; Retina, vol. 26, No. 6; Jul.-Aug. 2006; pp. 637-644; [downloaded 1-page abstract from Internet at http://www.ncbi.nim.nih.gov/pubmed/16829805] on Aug. 8, 2014.

Shukla, D.; "A comparison of brilliant blue G, trypan blue, and indocyanine green dyes to assist internal limiting membrane peeling during macular hole surgery"; Retina, vol. 31, No. 10; Nov. 2011; pp. 2012-2015; [downloaded 1-page abstract from internet at http://www.ncbi.nim.nih.gov/publmed/21685824] on Aug. 8, 2014.

Kim, Judy E.; "The role of ICG in Macular Hole Surgery"; Retinal Physician; Oct. 1, 2004; [downloaded from internet at http://www.retinalphysician.com/articleviewer.aspx?articleid+100033] on Aug. 8, 2014; pp. 1-4.

German Office Action in corresponding German Application No. 10 2013 009 817 .3 dated Mar. 14, 2013.

MICROSCOPY SYSTEM FOR OBSERVING FLUORESCENCE IN OPHTHALMOLOGY

CROSS-REFERENCES TO RELATED APPLICATIONS

The present application claims priority of Patent Application No. 10 2013 009 817.3, filed Jun. 11, 2013 in Germany, the entire contents of which are incorporated by reference herein.

FIELD

The present invention relates to an ophthalmology microscopy system particularly applicable for observing fluorescent radiation in eyes.

BACKGROUND

In ophthalmology, surgical microscopes tailored to the requirements of ophthalmology are frequently used for diagnostic purposes and during surgical interventions. Such surgical microscopes (operating microscopes) are also referred to as ophthalmology surgical microscopes.

Ophthalmology surgical microscopes are optical reflected-light microscopes used during surgical interventions and providing a magnification of typically between 5× and 30×. Surgical microscopes have, as compared to other optical reflected-light microscopes, an objective (objective lens system) with a larger focal length of typically between 175 mm and 550 mm. Characteristic for ophthalmology surgical microscopes is hereby that they often do not directly image an eye's ocular fundus, but indirectly by imaging an intermediate image of the eye which is produced by the eye lens and an ophthalmoscope lens located in the vicinity of the eye. The ophthalmoscope lens is hereby positioned at a distance of 4 mm to 80 mm to the eye's lens. The ophthalmoscope lens may be attached to the ophthalmology surgical microscope in at least one of a pivotable, removable and exchangeable manner. In surgical microscopes, the field of view, i.e. the area in the focal plane from which at least one optical imaging path of the microscope can produce an image at a certain point in time onto the retina of a user of the microscope, is typically larger than 1 mm². The field of view of a surgical microscope therefore comprises not only one single image point as is the case with scanning microscopes; rather, a multidimensional (especially two or three dimensional) image of the object observed with the surgical microscope is produced at each point in time.

To provide a user with a three dimensional impression of the object to be imaged, which is particularly important with eye surgery, ophthalmology surgical microscopes are often configured as stereo(scopic) microscopes simultaneously providing a pair of optical imaging paths to the eyes of a user. The optical imaging paths of the pair of optical imaging paths intersect near the focal plane of the surgical microscope at a stereoscopic angle of between 3° and 14°.

In ophthalmology surgical microscopes, the image of the object produced with the surgical microscope is provided to a user either by means of an eyepiece (or a pair of eyepieces in stereoscopic surgical microscopes) or is converted into electrical signals using an image converter (or a stereo image converter or a pair of image converters in stereoscopic surgical microscopes), and presented to a user, in addition or alternatively to the eyepieces, on at least one of a monitor and a head-mounted display.

In order to satisfy the ophthalmological requirements, ophthalmology surgical microscopes often comprise an integrated slit lamp and/or a keratoscope.

In ophthalmology it is occasionally necessary to render visible by dyes areas of a patient's eye to be observed. It is for example known to stain the epiretinal (limiting) membrane between the retina and the vitreous body, which itself is colorless and transparent, with indocyanine green, brilliant blue or trypan blue, since these dyes stain the limiting membrane more easily than the adjacent retina and the adjacent vitreous body. The problem is, however, that the respective biocompatibility of the dyes used and in particular that of indocyanine green often allows for only a low dose.

Some of the dyes used in ophthalmology are so called fluorescence dyes which, apart from the general characteristic of dyes of either absorbing or reflecting light of different wavelengths, absorb light of a first wavelength range (the so called excitation band) and convert it into light of a second wavelength range (the so called fluorescence band) different to the first wavelength range. Indocyanine green, for example, absorbs light of a wavelength range from 600 nm to 900 nm, and emits fluorescence in a wavelength range of 750 nm to 950 nm.

SUMMARY

Embodiments concern an ophthalmology microscopy system that enables a visualization of structures in an eye by observing fluorescent radiation in the eye with the aid of dyes in low doses in a particularly efficient manner.

Primarily, it is not the fluorescence dye's color nature of absorbing or reflecting light of different wavelength that is supposed to be observed with the ophthalmology microscopy system, but the fluorescent radiation of the fluorescence dye. Since the fluorescence band (wavelength range of the fluorescent radiation) of a fluorescence dye is, with respect to the excitation band (wavelength range in which the fluorescence dye absorbs radiation and converts the radiation absorbed into fluorescent radiation) of the same fluorescence dye, usually shifted towards longer wavelengths, wavelength ranges exist, where the fluorescent radiation does not overlap with the excitation radiation. Fluorescent radiation observed in these non-overlapping wavelength ranges is only attributed to the presence of an excited fluorescence dye and there is no mixing with excitation radiation thus providing a detection of the fluorescence dye on the basis of its fluorescence at already low doses of the fluorescence dye.

For observing fluorescence, the ophthalmology microscope system comprises according to embodiments an imaging system and a first illumination system.

The imaging system provides at least one optical imaging path producing a multi-dimensional (in particular two or three dimensional) magnified image of an object disposed or disposable in a focal plane of the imaging system. The object itself is not part of the ophthalmology microscopy system. As a result, the at least one optical imaging path comprises a section located with respect to the traveling direction of radiation propagating through the at least one optical imaging path on the object side, where the at least one optical imaging path intersects the focal plane of the imaging system. The imaging system comprises at least one optical observation filter which may for instance be a transmission filter or a reflection filter. The imaging system may for instance further comprise at least one objective lens. The optical axis of the at least one objective lens intersects the focal plane.

The first illumination system provides a first illumination beam path intersecting the focal plane of the imaging system at a variable angle of less than 90°, and in particular of less than 80°, and further in particular of less than 75°. This variable angle may for instance be measured relative to the central ray of the radiation passing the first illumination beam path. Accordingly, also the optical imaging path and the first illumination beam path may be arranged at a variable angle with respect to each other, when the central ray of the radiation passing the at least one optical imaging path intersects the central ray of the radiation passing the first illumination beam path. Also the first illumination system may comprise at least one optical lens. The optical axis of the at least one optical lens intersects the focal plane of the imaging system at the variable angle.

The microscopy system as a whole is switchable between at least two different operating states. Accordingly, also the imaging system and the first illumination system comprise at least two different operating states. The operating states of the imaging system and the first illumination system are coordinated with one another.

In the first operating state of the microscopy system, radiation passing the first illumination beam path includes, at least in a section along the illumination beam path in traveling direction of the radiation, a spectrum free of a pass band of the at least one observation filter. Accordingly, also the illumination radiation incident on the object observed has a spectrum free of a pass band of the observation filter. The at least one optical observation filter of the imaging system is further disposed in the at least one optical imaging path. Radiation passing the at least one optical imaging path thus has, with respect to the traveling direction of the radiation, different spectra before and after the at least one observation filter. Accordingly, the first operating state enables an observation of fluorescence of the object observed by the imaging system, provided the fluorescence band of the fluorescence (and thus of a fluorescence dye used) is within the pass band of the at least one observation filter.

The pass band of a filter is hereby understood to be a wavelength range, within which more than 60%, and in particular more than 80% of the incident radiation is transmitted.

In the second operating state of the microscopy system, radiation passing the first illumination beam path and being incident on the object observed has a spectrum having a bandwidth of at least 200 nm, and in particular of at least 250 nm and being in the range of 380 nm to 780 nm. According to an embodiment, the object observed is illuminated with white light (being polychromatic light).

In the second operating state, the at least one optical observation filter of the imaging system may be located outside of the at least one optical imaging path. Alternatively, the at least one optical observation filter may be arranged such that part of the radiation passing the optical imaging path bypasses the at least one optical observation filter. Thus, at least in the second operating state, the at least one observation filter does not affect the spectrum of at least a part of the radiation passing the at least one optical imaging path, so that an observation of the object to be observed can be carried out with white light, as the white light can be observed by a user of the microscope system via the imaging system.

According to an embodiment, the at least one observation filter has a pass band corresponding to the fluorescence band of the fluorescence dye used for staining the object observed. According to this embodiment, the illumination radiation of the first illumination beam path incident on the object observed does not contain the fluorescence band of the fluorescence dye in the first operating state. The illumination radiation incident on the object observed in the first operating state includes an excitation band of the fluorescence dye instead. The pass band of the at least one observation filter is thus adapted, and may in particular correspond, to the fluorescence band of the fluorescence dye, and the spectrum of the illumination radiation is adapted, and may in particular correspond, to the excitation band of the same fluorescence dye.

According to an embodiment, the at least one observation filter has a stop band corresponding to the frequencies other than the fluorescence band of the fluorescence dye used for staining the object observed.

According to an embodiment, the at least one observation filter is a bandpass filter having one pass band corresponding to the fluorescence band of the fluorescence dye used for staining the object observed, a first stop band corresponding to frequencies lower than the fluorescence band of the fluorescence dye used for staining the object observed and a second stop band corresponding to frequencies higher than the fluorescence band of the fluorescence dye used for staining the object observed. According to an embodiment, the properties of the bandpass filter regarding frequencies outside the frequency band of visible light and especially frequencies below the near ultraviolet band and/or above the near infrared band are ignored.

According to an embodiment, radiation passing the first illumination beam path in the first operating state includes, at least in a section facing the object in the traveling direction of the radiation, a spectrum having a bandwidth of not more than 150 nm, and in particular not more than 100 nm, and further in particular of not more than 50 nm. Even monochromatic light might be used, for example.

The bandwidth of a spectrum is hereby understood as the wavelength range extending between wavelengths of the spectrum with the wavelengths being spaced apart maximally, and with an intensity of the radiation being at least 10% of a maximum radiation intensity within the spectrum.

According to an embodiment, the first illumination system comprises a handle piece comprising a rigid light guide. Thus, the rigid light guide is supported by the handle piece. The end of the rigid light guide facing away from the handle piece may be configured to directionally or diffusely output radiation passing the rigid light guide.

According to an embodiment, the rigid light guide is configured for being disposed in a visceral cavity and/or a hollow organ and/or a vitreous body of an eye ball. For this purpose, the rigid light guide may be configured for piercing parts of the human body neighboring the visceral cavity, hollow organ or vitreous body, respectively, such as the sclera and choroidea of the eye, for example.

According to an embodiment, the first illumination system comprises a handle piece and a flexible light guide connecting the handle piece to at least one radiation source. In particular at its end facing away from the flexible light guide, the handle piece further comprises a rigid light guide optically connected to the flexible light guide. The connection between the flexible light guide and the rigid light guide may be located inside the handle piece. The rigid light guide may be configured for being disposed in the vitreous body of an eye ball and, as the case may be, for piercing the sclera and choroidea of the eye. The first illumination system may therefore be an endoilluminator enabling an illumination of the eye from inside. The end of the rigid light guide facing away from the handle piece may be configured to directionally and diffusely output radiation passing the rigid light guide.

According to an embodiment, the at least one radiation source of the first illumination system is incorporated into a housing of the microscopy system that also accommodates the imaging system. According to an alternative embodiment, a housing separated from the housing accommodating the imaging system accommodates the at least one radiation source of the first illumination system.

According to an alternative embodiment, the first illumination system comprises a handle piece and a radiation source incorporated into the handle piece, with the handle piece further comprising a rigid light guide optically connected to the radiation source. The first illumination system may thus be configured as an endoilluminator having a radiation source incorporated into the handle piece.

With the first illumination system being configured as an endoilluminator, it is possible to direct—depending on the operating state of the microscopy system—radiation corresponding to the excitation band of a fluorescence dye or white light specifically onto an area of interest inside a visceral cavity, hollow organ (for example the eye) or vitreous body without causing reflections (for example on the eye lens). Further, the radiation may thus be directed to desired regions only and with as little intensity as possible.

According to an embodiment, the first illumination system comprises a first radiation source and an illumination filter. In the first and second operation conditions, the radiation source emits radiation with a spectrum having a bandwidth of at least 200 nm, and in particular of at least 250 nm, and being in the range from 380 nm to 780 nm. The illumination filter comprises a stop band (blocking band) corresponding to the pass band of the observation filter. A stop band of a filter is hereby to be understood as the wavelength range in which less than 60%, and in particular less than 20%, and further in particular less than 5% of an incident radiation (e.g. light) are transmitted. The illumination filter may for instance have a pass band being only transparent for radiation of wavelengths shorter than the pass band of the observation filter. In the first operating state of the microscopy system, the illumination filter is disposed in the first illumination beam path, and in the second operating state of the microscopy system, the illumination filter is disposed outside of the first illumination beam path. The first radiation source thus emits white light in both operating states, and the spectrum desired for the radiation incident on the object to be observed is adjusted by swinging the illumination filter in and out.

According to an alternative embodiment, the first illumination system comprises a first radiation source and a second radiation source. In the first operating state of the microscopy system only the first radiation source is used and thus emits radiation, and in the second operating state of the microscopy system only the second radiation source is used and thus emits radiation. The first radiation source hereby emits only radiation having a spectrum free of the pass band of the observation filter, and having in particular a bandwidth of not more than 150 nm, and further in particular of not more than 100 nm, and further in particular of not more than 50 nm. The first radiation source may even emit monochromatic light, for example. The second radiation source emits radiation having in particular a continuous (and thus polychromatic) spectrum with a bandwidth of at least 200 nm, and in particular of at least 250 nm, and being in the range from 380 nm to 780 nm. The second radiation source thus emits white light. The spectrum of the radiation emitted from the second radiation source may include the pass band of the observation filter completely or in part. The desired spectrum of the radiation directed onto the object to be observed in the respective operating state is thus adjusted by selecting different radiation sources.

If the at least one observation filter in the at least one optical imaging path and an illumination filter in the first illumination beam path of the first illumination system or an appropriate selection of the radiation source of the first illumination system ensure that the excitation band and fluorescence band of a dye, with which an object to be observed is stained, do not overlap, the radiation passing the at least one optical imaging path finally results from the fluorescence of the fluorescence dye only. Hence, the fluorescence dye can even be localized at a low dose.

According to an embodiment, the ophthalmology microscopy system further comprises a second illumination system providing a second illumination beam path intersecting the focal plane of the imaging system at a constant angle of more than 80°, and in particular more than 85°, and further in particular of 90°. Accordingly, central rays of the second illumination path and of the at least one optical imaging path are arranged at an angle of less than 20°, and in particular less than 10°.

According to an embodiment, the second illumination system comprises a radiation source different from a radiation source of the first illumination system.

According to an embodiment, the second illumination beam path of the second illumination system passes through an objective lens of the imaging system. This enables an illumination of the object to be observed at a smallest possible angle between central rays of the second illumination beam path and the at least one optical imaging path.

According to an embodiment, the ophthalmology microscopy system further comprises a controller which is connected to the imaging system and the first illumination system and which is configured to optionally switch the imaging system and the first illumination system simultaneously either into the first or the second operating states. As a consequence, it is possible to dispose the at least one observation filter in the at least one optical imaging path and to adapt the radiation passing through the first illumination beam path correspondingly using the controller.

According to an embodiment, the controller is further connected to the second illumination system and is further configured to alternatively actuate the first illumination system and the second illumination system.

According to an embodiment, the connection of the controller to the imaging system and the first illumination system is implemented using electrical lines or optical fibers. According to an alternative embodiment, the connection of the controller to the imaging system and/or the first illumination system is implemented using a radio interface, such as Bluetooth or WLAN, for example.

According to an embodiment, the imaging system further comprises at least one image sensor located in the image plane of the imaging system and outputting image data representing the image produced from the object by the imaging system. Said image sensor may for instance be a CCD sensor or a CMOS sensor. According to an embodiment, the image sensor is adapted to receive radiation in the near-infrared range and to output respective image data. This way, it is possible to display near-infrared fluorescent radiation. According to an embodiment, the controller of the microscopy system is adapted to detect and segment (free-form selecting) the fluorescence in the image data using digital image processing. The thus free-form selected fluorescence may be amplified and superimposed on the image data produced with white light.

According to an embodiment, the imaging system provides at least one pair of optical imaging paths intersecting in the focal plane of the imaging system at a stereoscopic angle of between 3° and 14°. Each optical imaging path produces a magnified multi-dimensional (in particular two or three dimensional) image of the object disposable in the focal plane of the imaging system. The ophthalmology microscopy system may thus form a stereo microscope.

According to an embodiment, the imaging system comprises an objective having at least two optical lenses through which the at least one optical imaging path passes consecutively, and which are moveable with respect to each other for changing a position of the focal plane of the imaging system.

According to an embodiment, the imaging system includes a zoom (zoom lens system) comprising at least three optical lenses, with the optical lenses of the zoom being consecutively passed through by the at least one optical imaging path, and with at least two distances between the optical lenses being modifiable for changing a magnification of the imaging system.

According to an embodiment, the imaging system comprises an objective having at least one optical objective lens and one ophthalmoscope lens. When the ophthalmoscope lens is used, the optical axis of the ophthalmoscope lens is hereby identical to the optical axis of the at least one objective lens, and the ophthalmoscope lens is spaced apart from the nearest objective lens by at least 150 mm.

According to an embodiment, all optical elements of the microscopy system are provided with an antireflection coating.

In this context, it is noted that the terms "including", "comprising", "containing", "having" and "with", as well as grammatical modifications thereof used in this specification or the claims for listing features, are generally to be considered to specify a non-exhaustive listing of features such as method steps, components, ranges, dimensions or the like, and do by no means preclude the presence or addition of one or more other features or groups of other or additional features.

BRIEF DESCRIPTION OF THE DRAWINGS

Further features of the invention will be apparent from the following description of exemplary embodiments together with the claims and the Figures. In the Figures, like or similar elements are designated as far as possible by alike or similar reference numerals. It is noted that the invention is not limited to the embodiments of the exemplary embodiments described, but is defined by the scope of the attached claims. In particular, embodiments according to the invention may implement individual features in a different number and combination than the examples provided below, whereby it is further noted that not all possible embodiments necessarily exhibit each and every, or any, of the advantages identified herein. Therefore, to understand the features of the individual components of a specific embodiment, the descriptions of other embodiments and of the summary of the disclosure should be referred to.

In the following explanation of exemplary embodiments of the invention, reference is made to the enclosed Figures, of which

DETAILED DESCRIPTION OF EXEMPLARY EMBODIMENTS

Figure 1:
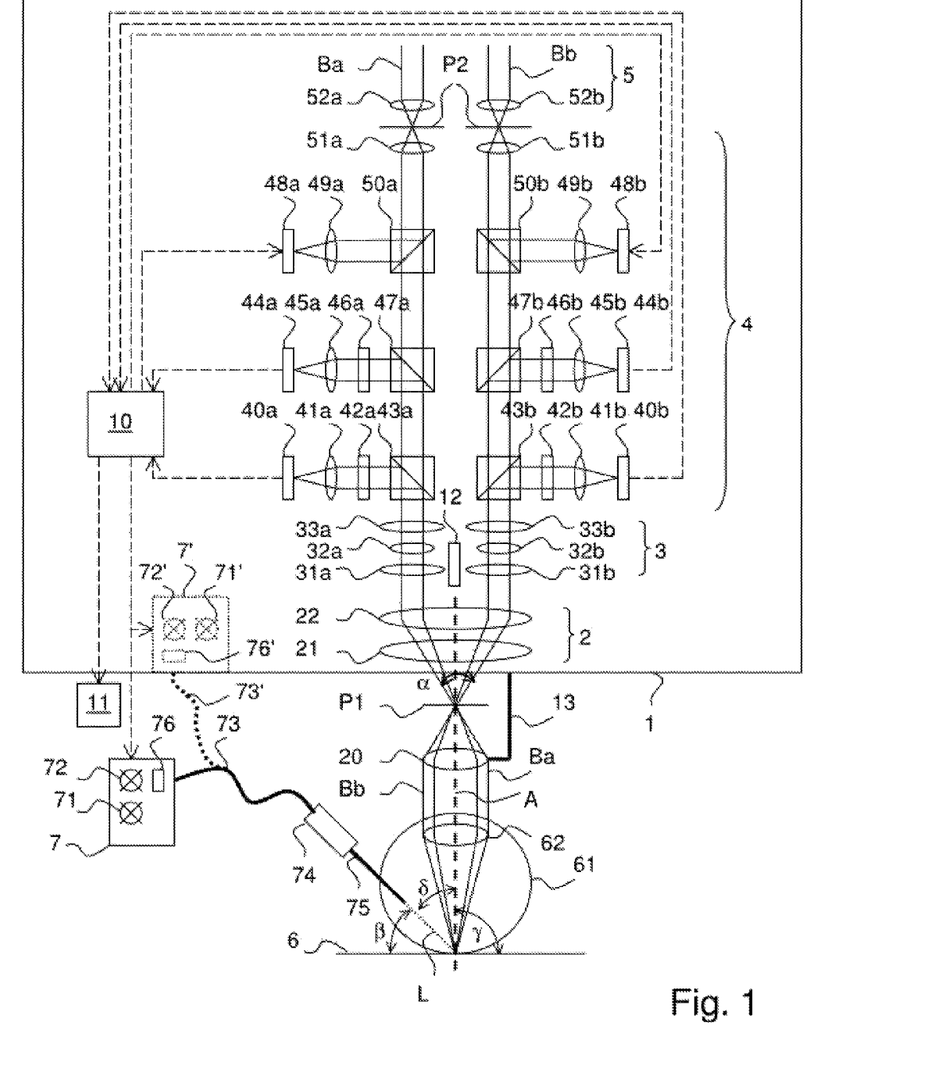
FIG. 1 shows a schematic representation of a configuration of an ophthalmology microscopy system according to an embodiment.

The ophthalmology microscopy system comprises a housing 1 accommodating an imaging system comprised of an objective (objective lens system) 2, a zoom (zoom lens system) 3, an optical tube (lens barrel system/tubular system) 4, and an eye piece (eye piece system) 5. The housing further supports an ophthalmoscope lens 20 also being part of the imaging system. The imaging system provides two optical imaging paths Ba, Bb, consecutively running through the ophthalmoscope lens 20, the objective 2, the zoom 3, the optical tube 4, and the eye piece 5.

The ophthalmoscope lens 20 is supported on the housing 1 by a mount 13. Together with a lens 62 of an eye to be observed the ophthalmoscope lens 20 produces a magnified first intermediate image P1 of an eye's 61 epiretinal limiting membrane located in the focal plane 6.

The optical imaging paths Ba, Bb intersect in a focal plane of the objective 2, where the first intermediate image P1 is formed, at a stereoscopic angle α. This stereoscopic angle is measured between the central rays (not shown in FIG. 1) of the optical imaging paths Ba, Bb. The stereoscopic angle α amounts to between 6° and 10°, depending on the respective working distance of the objective 2. The stereoscopic optical imaging paths Ba, Bb each produce a magnified two dimensional image of the intermediate image P1, and thus an image of the eye's 61 epiretinal limiting membrane located in the focal plane 6, so that altogether a magnified three dimensional image impression is achieved by viewing both optical imaging paths.

In the embodiment shown, the objective 2 is implemented in the form of a two-part structure and comprises two optical lenses 21, 22, consecutively passed through by the stereoscopic optical imaging paths Ba, Bb. Hereby, both stereoscopic optical imaging paths Ba, Bb together pass through the optical lenses 21, 22. The distance between the optical lenses 21, 22 is shiftable along their optical axis A for adjusting a position of the focal plane of the objective 2. In the embodiment shown, the working distance of the objective 2, and thus the distance of the first intermediate image P1 to the lens vertex of the optical lenses 21 of the objective 2 located along the stereoscopic optical imaging paths Ba, Bb closest to the first intermediate image is between 150 mm and 200 mm. The optical lenses 21, 22 of the objective 2 produce an image of the first intermediate image P1 at infinity so that an afocal interface is located between the objective 2 and the zoom 3. It is noted that the present invention is not limited to two-part objectives or afocal objectives, and that multi-part objectives and also non-afocal objectives may generally be used instead.

In the embodiment shown, the zoom 3 is implemented in the form of a three-part structure and comprises three pairs of optical lenses 31a, 31b, 32a, 32b, 33a, 33b, being passed through consecutively by one of the two stereoscopic optical imaging paths Ba, Bb. The stereoscopic optical imaging paths Ba, Bb thus each pass the zoom 3 in separate optical lenses 31a, 32a, 33a or 31b, 32b, 33b. To change the magnification, the distance between the optical lenses 31a, 32a, 33a or 31b, 32b, 33b, respectively, is displaceable along their optical axes (not shown). It is noted that the present invention is not limited to three-part zooms, and that in general multi-part zooms may used. Also the zoom 3 produces an image of both stereoscopic optical imaging paths Ba, Bb at infinity, so that an afocal interface is also located between the zoom 3 and the optical tube 4.

Along each of the two stereoscopic optical imaging paths Ba, Bb, the optical tube 4 comprises three consecutively passed through first, second, and third beam splitters 43a, 47a, 50a and 43b, 47b, 50b as well as tubular lenses 51a, 51b. The first and second beam splitters 43a, 43b, 47a, 47b are hereby oriented such that they split out a portion of the radiation passing through the respective optical imaging path Ba, Bb. The third beam splitters 50a, 50b are oriented such that they superimpose further radiation on the radiation passing through the respective optical imaging path Ba, Bb. The first through third beam splitters 43a, 47a, 50a or 43b, 47b, 50b, respectively, and the tubular lenses 51a, 51b are each passed through by only one of the two stereoscopic optical imaging paths Ba, Bb.

The first beam splitters 43a, 43b direct a portion of the radiation passing through the respective optical imaging path Ba, Bb via a respective observation filter 42a, 42b and a camera optical system 41a, 41b to an infrared camera 40a, 40b. The infrared cameras 40a, 40b output image data representing the image of the eye's 61 epiretinal limiting membrane produced in the infrared by the ophthalmoscope lens 20, the objective 2, and the zoom 3, and also the camera optical system 41a, 41b. The infrared cameras 40a, 40b are in the present case configured as removable units.

The second beam splitters 47a, 47b direct a portion of the radiation passing through the respective optical imaging path Ba, Bb via a respective infrared blocking filter 46a, 46b and a camera optical system 45a, 45b to a color camera 44a, 44b. The color cameras output image data representing the image of the eye's 61 epiretinal limiting membrane produced in the visible range by the ophthalmoscope lens 20, the objective 2, and the zoom 3, and also the camera optical system 45a, 45b. The infrared blocking filters 46a, 46b hereby ensure that no near-infrared radiation is incident on the color cameras 44a, 44b, since this may produce wrong colors. It is noted that the infrared blocking filters 46a, 46b are only optional. The infrared blocking filters 46a, 46b may further be incorporated into the color cameras 44a, 44b. In the present case, the color cameras are configured as removable units.

The third beam splitters 50a, 50b each superimpose an image shown on one of the LCD displays 48a, 48b onto the radiation passing through the respective optical imaging path Ba, Bb. To this end, an appropriate optical system 49a, 49b is respectively provided between the LCD display 48a, 48b and the associated third beam splitter 50a, 50b.

Each lens 51a, 51b of the optical tube produces a second intermediate image P2 of the two stereoscopic optical imaging paths Ba, Bb.

The second intermediate images P2 may be viewed by a user through optical lenses 52a, 52b of the eye piece 5.

It is noted that the optical lenses of the imaging system may be simple lens elements or cemented elements, with the cemented elements being formed by bonding at least two optical lenses made from materials with different refractive indices permanently flat to each other.

The ophthalmology microscopy system further comprises a first radiation source in the form of an endoilluminator 7. In the embodiment shown, the endoilluminator 7 comprises a handle piece 74 connected to a housing of the endoilluminator 7 by a flexible light guide 73, with the housing accommodating a LED (light emitting diode) 71 and a xenon lamp 72, and a switchable illumination filter 76. At the end facing away from the flexible light guide 73, the handle piece 74 comprises a rigid light guide 75. The rigid light guide 75 is attached to the handle piece 74 and supported by the handle piece 74. The rigid light guide 75 is optically connected to the flexible light guide 73, and the flexible light guide 73 is optically connectable to the LED 71 or the xenon lamp 72, whereby the illumination filter 76 is disposable between the flexible light guide 73 and the xenon lamp 72. The radiation emitted from the xenon lamp 72 has a bandwidth of 400 nm, and the radiation emitted from the LED 71 has a bandwidth of 50 nm. The rigid light guide 75 is adapted for piercing the sclera and choroidea of the eye 61 such that the end of the rigid light guide 75 facing away from the handle piece may be disposed inside the vitreous body of the eye 61. The radiation output at this end of the rigid light guide 75 defines a first illumination beam path L. The central ray of this first illumination beam path L intersects the focal plane 6 of the ophthalmoscope lens 20 at a variable angle 13 of, in the present case, approximately 60°. Hence, the angle δ between the central ray of this first illumination beam path L and the optical axis of the ophthalmoscope lens 20 and of the optical lenses 21 and 22 of the objective 2 is also variable and in the present case around 30°.

It is noted that the LED 71 and/or the xenon lamp 72 and the illumination filter 76 may alternatively also be incorporated into the handle piece 74, so that the housing of the endoilluminator 7 and the handle piece 74 may be one, and the flexible light guide 73 may be dispensed with.

It is further noted that the illumination filter is only required for the endoilluminator comprising a broadband radiation source (e.g. a xenon lamp). Thus, either the narrow-band radiation source (e.g. the LED) or the illumination filter is optional.

Finally it is noted that the radiation source of the endoilluminator may alternatively also be incorporated into the housing accommodating the imaging system. The flexible light guide is then connected to this housing. This is shown schematically in FIG. 1 by elements 7', 71', 72', 76', and 73'.

The housing 1 further accommodates a xenon lamp 12 providing a second illumination beam path. In the embodiment shown, the second illumination beam path is oriented coaxially to the optical axis A of the optical lenses 21 and 22 of the optical lens system 2 and the ophthalmoscope lens 20, and thus passing through these. The optical axis A and the second illumination beam path form with the focal plane 6 of the ophthalmoscope lens 20 a constant angle γ of 90°. The radiation emitted by the xenon lamp 12 has a bandwidth of 400 nm. It is noted that the xenon lamp 12 is only optional. A halogen lamp or another white light source such as a LED may be used instead.

Finally, the housing accommodates a controller 10 connected by control lines illustrated by dashed lines to the infrared cameras 40a, 40b, the color cameras 44a, 44b, and the LCD displays 48a, 48b, and also to an external 3D-monitor 11 and the endoilluminator 7.

In the following, the operation of the above ophthalmology microscopy system is described for an exemplary observation of an epiretinal limiting membrane stained with indocyanine green. The epiretinal limiting membrane is located between the retina and the vitreous body of a patient's eye. However, it is noted that the present invention is not limited to a use of indocyanine green. Instead, any fluorescence dye allowed for the respective usage may be used. Further, the invention is not limited to an observation of the eye's epiretinal limiting membrane, but may generally be used for observing fluorescence in a body cavity, visceral cavity, hollow organ and vitreous body, for example.

Figure 2A:
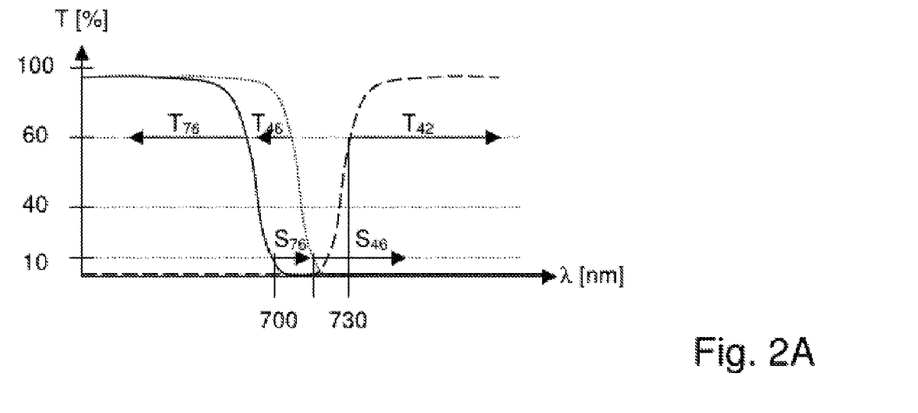
FIG. 2A shows a schematic representation of a pass band of an illumination filter, an observation filter, and an infrared blocking filter, that may be used in the ophthalmology microscopy system from FIG. 1.

According to a first embodiment, in the first operating state the controller 10 controls the endoilluminator 7 such that only the xenon lamp 72 is in operation, and the illumination filter 76 is located between the xenon lamp 72 and the flexible light guide 73. The xenon lamp 72 emits an almost continuous spectrum in a wavelength range of between 380 nm and 780 nm. The transmission behavior of the illumination filter 76 is illustrated schematically by a solid line in FIG. 2A. As can be seen, the illumination filter 76 has a stop band $S_{76}$ for wavelengths above 700 nm, where the filter is almost opaque, and a pass band $T_{76}$ for wavelengths below 690 nm, where the filter is almost transparent. Due to the use of the illumination filter 76, the eye's 61 epiretinal limiting membrane is irradiated via the flexible light guide 73 and the rigid light guide 75 with radiation in the wavelength range from 380 nm to 700 nm. This radiation contains a portion of the excitation band of indocyanine green.

At the same time, the controller 10 controls the color cameras 44a and 44b according to the first embodiment such that an image of the epiretinal limiting membrane of the eye 61 is produced. Since the radiation emitted by the xenon lamp 72 via the illumination filter 76 still covers a large portion of the visible light, color images may be obtained hereby that have no or only small color defects. Hereby, the infrared blocking filters 46a, 46b ensure that no infrared radiation and thus substantially no fluorescent radiation from indocyanine green reaches the receiving areas of the color cameras 44a, 44b. The transmission behavior of the infrared blocking filters 46a, 46b is illustrated schematically in FIGS. 2A and 2B by dotted lines. As can be seen, the infrared blocking filters 46a, 46b have a pass band $T_{46}$ for wavelengths below 700 nm, where the filters are almost transparent, and a stop band $S_{46}$ for wavelengths above 720 nm, where the filters are almost opaque. From the image data output by the color cameras 44a, 44b, the controller generates a three dimensional image of the epiretinal limiting membrane of the eye 61, and outputs this image to a 3D monitor 11 and the LCD displays 48a, 48b. A user may thus view the three dimensional image either on the 3D monitor 11 or through the eye pieces 5. The controller 10 may further superimpose an image of the fluorescence to that image, as will be explained later.

Figure 2B:
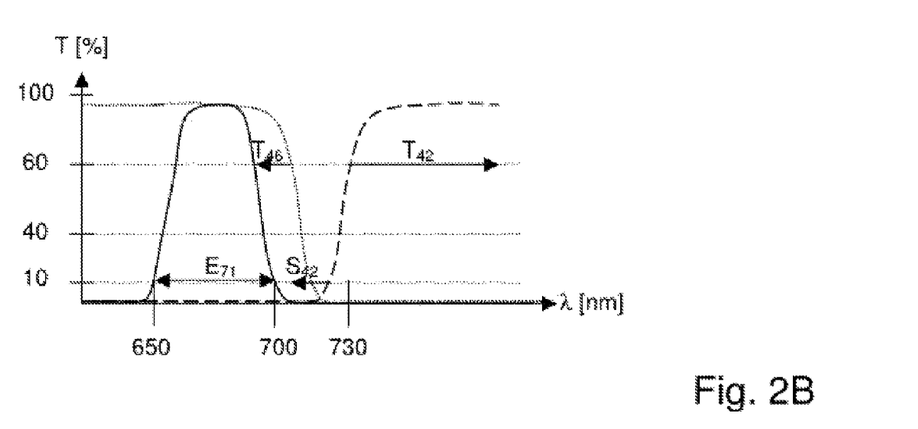
FIG. 2B shows a schematic representation of the pass band of an observation filter and an infrared blocking filter, and the spectrum of a radiation source, that may be used in the ophthalmology microscopy system from FIG. 1.

According to a second embodiment, in the first operating state the controller 10 controls the endoilluminator 7 such that only LED 71 is in operation illuminating the eye's 61 epiretinal limiting membrane via the flexible light guide 73 and the rigid light guide 75 with radiation in the wavelength range from 650 nm to 700 nm. The radiation output by LED 71 thus includes a portion of the excitation band of indocyanine green. The emission spectrum $E_{71}$ of LED 71 is illustrated in FIG. 2B schematically by a solid line.

At the same time, the controller 10 controls the infrared cameras 40a and 40b in both embodiments such that the fluorescence caused by excitation of indocyanine green with the illumination radiation is detected. The observation filters 42a, 42b hereby ensure that the receiving areas of the infrared cameras 40a and 40b receive only the fluorescent radiation from indocyanine green, while other wavelength ranges are blocked. The transmission behavior of the observation filters 42a, 42b is illustrated schematically in FIGS. 2A and 2B by a dashed line. As can be seen, the observation filters 42a, 42b are almost transparent for wavelengths above 730 nm in a pass band $T_{42}$, and are almost opaque for wavelengths below 720 nm in a stop band $S_{42}$. The controller 10 detects the fluorescence in the image data output by infrared cameras 40a and 40b by digital image processing and isolates the fluorescence in the image by free-form selection. The controller 10 then creates a three dimensional image of the fluorescence and outputs it to the 3D monitor 11 and to the LCD displays 48a, 48b. If applicable, the controller hereby superimposes a two or three dimensional image of the eye's 61 epiretinal limiting membrane generated based on color cameras 44a, 44b. A user may thus observe the fluorescence either on the 3D monitor 11 or through the eyepieces 5.

In the second operating state, the controller 10 controls the endoilluminator 7 according to a first embodiment such that only the xenon lamp 72 is in operation and the illumination filter 76 is located outside of the beam path between the xenon lamp 72 and the flexible light guide 73. Thus, the eye's 61 epiretinal limiting membrane is irradiated by the flexible light guide 73 and the rigid light guide 75 with radiation in the wavelength range from 380 nm to 780 nm and thus with white light.

According to a second embodiment, in the second operation state the controller is configured to operate the xenon lamp 12 and to illuminate the epiretinal limiting membrane of the eye 61 with white light. The endoilluminator 7 may then be turned off and not emit light in the second operating state.

Accordingly, it is possible in both embodiments to generate an image of the epiretinal limiting membrane of the eye 61 accurate in colors using the color cameras 44a and 44b, and to output the image of the epiretinal limiting membrane via monitor 11. Further, a previously generated image of the fluorescence, isolated by free-form selection, may be overlaid in the correct position by the controller using LCD displays 48a, 48b.

The controller may be adapted to switch between the two operating states in intervals of less than 1/10 second. This switching is hardly recognized by a user looking only through the eyepiece 5. A direct visual observation of the fluorescence via eyepieces 5 is not possible, since the other light is too bright for the fluorescence to be seen. However, with the controller 10 being configured to isolate the fluorescence in the image data output from infrared cameras 40a, 40b, amplify it, and overlay it via LCD displays 48a, 48b to the optical imaging paths Ba, Bb, an indirect visual observation of the overlaid fluorescence via the eyepieces 5 is enabled.

Although a use of infrared cameras 40a, 40b and color cameras 44a, 44b is described above, only one camera pair may alternatively be used that may electively record near-infrared radiation and visible light by using a filter (for instance a Bayer-filter).

Although a stereo microscopy system having a pair of stereoscopic optical imaging paths Ba, Bb is described above, the present invention is not limited hereto. Alternatively several pairs of stereoscopic optical imaging paths may be provided. Further alternatively, the microscopy system may also be a monoscopic system having only one optical imaging path.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An ophthalmology microscopy system for observing fluorescence, comprising:
    an imaging system providing at least one optical imaging path producing a magnified multi-dimensional image of an object disposable in a focal plane of the imaging system, with the imaging system comprising at least on optical observation filter; and
    a first illumination system providing a first illumination beam path intersecting the focal plane of the imaging system at a variable angle of less than 90°, or less than 80°, or less than 75°;
    wherein the microscopy system comprises first and second operating states;
    wherein radiation passing through the first illumination beam path in the first operating state has at least in a section along the illumination beam path a spectrum being free of a pass band of the observation filter; and
    wherein radiation passing through the first illumination beam path in the second operating state has a spectrum with a bandwidth of at least 200 nm, or at least 250 nm, and being in a range from 380 nm to 780 nm,
    wherein the first illumination system comprises a handle piece comprising a rigid light guide,
    wherein the rigid light guide is configured for being disposed in at least one of a visceral cavity, hollow organ and vitreous body of an eye ball.

2. The ophthalmology microscopy system of claim 1, wherein the rigid light guide is configured for piercing parts of the human body neighboring at least one of the visceral cavity, hollow organ or vitreous body.

3. The ophthalmology microscopy system of claim 2, wherein the first illumination system further comprises:
    a flexible light guide connecting the handle piece to at least one radiation source;
    wherein the rigid light guide is attached to the handle piece and is optically connected to the flexible light guide.

4. The ophthalmology microscopy system of claim 2, wherein the first illumination system further comprises:
    a radiation source incorporated into the handle piece;
    wherein the rigid light guide is optically connected to the radiation source.

5. The ophthalmology microscopy system of claim 1, wherein the first illumination system further comprises:
    a flexible light guide connecting the handle piece to at least one radiation source;
    wherein the rigid light guide is attached to the handle piece and is optically connected to the flexible light guide.

6. The ophthalmology microscopy system of claim 1, wherein the first illumination system further comprises:
    a radiation source incorporated into the handle piece;
    wherein the rigid light guide is optically connected to the radiation source.

7. The ophthalmology microscopy system of claim 1, wherein the at least one radiation source of the first illumination system is received in a housing of the microscopy system that also receives the imaging system.

8. The ophthalmology microscopy system of claim 1, wherein the at least one radiation source of the first illumination system is received in a housing that is separate from a housing accommodating the imaging system.

9. The ophthalmology microscopy system of claim 1, wherein the first illumination system comprises a first radiation source and an illumination filter;
    wherein in the first and second operating states the radiation source emits radiation with a spectrum having a bandwidth of at least 200 nm, or radiation with a spectrum having a bandwidth of at least 250 nm, the radiation emitted by the radiation source being in a range from 380 nm to 780 nm;
    wherein the illumination filter has a stop band comprising the pass band of the observation filter; and
    wherein in the first operating state the illumination filter is located in the first illumination beam path, and in the second operating state the illumination filter is located outside of the first illumination beam path.

10. The ophthalmology microscopy system of claim 9, further comprising a controller connected to the imaging system and the first illumination system and adapted to optionally switch the imaging system and the first illumination system simultaneously either into the first or the second operating state.

11. The ophthalmology microscopy system of claim 1,
    wherein the first illumination system comprises a first radiation source and a second radiation source;
    wherein, in the first operating state, only the first radiation source is in operation, and in the second operating state, only the second radiation source is in operation,
    wherein the first radiation source emits radiation with a spectrum having a bandwidth of at least 200 nm, and in particular emits radiation with a spectrum having a bandwidth of at least 250 nm, the radiation emitted by the first radiation source being in a range from 380 nm to 780 nm; and
    wherein the second radiation source emits only radiation with a spectrum that is free from the pass band of the observation filter, and that comprises in particular a bandwidth of not more than 150 nm.

12. The ophthalmology microscopy system of claim 11, further comprising a controller connected to the imaging system and the first illumination system and adapted to optionally switch the imaging system and the first illumination system simultaneously either into the first or the second operating state.

13. The ophthalmology microscopy system of claim 1, further comprising a second illumination system providing a second illumination beam path intersecting the focal plane of the imaging system at a constant angle of more than 80°, or of more than 85°, or of more than 90°.

14. The ophthalmology microscopy system of claim 1,
    wherein the imaging system further comprises at least one imaging sensor disposed in an imaging plane of the imaging system and outputting image data representing the image of the object produced by the imaging system.

15. The ophthalmology microscopy system of claim 1,
    wherein the imaging system provides at least one pair of optical imaging paths intersecting in the focal plane of the imaging system at a stereoscopic angle of between 3° and 14° and producing a magnified multi-dimensional image of an object disposable in the focal plane of the imaging system.

16. The ophthalmology microscopy system of claim 1,
wherein the first illumination system and the imaging system each comprise a separate housing, with the housings being disposable independent from each other; and
wherein the illumination system and the imaging system are connectable to a shared controller of the ophthalmology microscopy system.

17. An ophthalmology microscopy system for observing fluorescence, comprising:
an imaging system providing at least one optical imaging path producing a magnified multi-dimensional image of an object disposable in a focal plane of the imaging system, with the imaging system comprising at least one optical observation filter; and
a first illumination system providing a first illumination beam path intersecting the focal plane of the imaging system at a variable angle of less than 90°;
wherein the microscopy system comprises first and second operating states;
wherein radiation passing through the first illumination beam path in the first operating state has at least in a section along the illumination beam path a spectrum being free of a pass band of the observation filter; and
wherein the first illumination system comprises:
a handle piece comprising a rigid light guide, wherein the rigid light guide is configured for piercing parts of the human body neighboring at least one of the visceral cavity, hollow organ or vitreous body;
a first radiation source incorporated into the handle piece; and
an illumination filter;
wherein the rigid light guide is optically connected to the radiation source;
wherein in the first and second operating states the radiation source emits radiation with a spectrum having a bandwidth of at least 200 nm, the radiation emitted by the radiation source being in a range from 380 nm to 780 nm;
wherein the illumination filter has a stop band comprising the pass band of the observation filter; and
wherein in the first operating state the illumination filter is located in the first illumination beam path, and in the second operating state the illumination filter is located outside of the first illumination beam path;
the ophthalmology microscopy system further comprising:
a second illumination system providing a second illumination beam path intersecting the focal plane of the imaging system at a constant angle of more than 80°, the second illumination system being located in the same housing as the imaging system; and
a controller connected to the imaging system and the first illumination system and adapted to optionally switch the imaging system and the first illumination system simultaneously either into the first or the second operating state.

18. An ophthalmology microscopy system for observing fluorescence, comprising:
an imaging system providing at least one optical imaging path producing a magnified multi-dimensional image of an object disposable in a focal plane of the imaging system, with the imaging system comprising at least one optical observation filter; and
a first illumination system providing a first illumination beam path intersecting the focal plane of the imaging system at a variable angle of less than 90°;
wherein the microscopy system comprises first and second operating states;
wherein radiation passing through the first illumination beam path in the first operating state has at least in a section along the illumination beam path a spectrum being free of a pass band of the observation filter; and
wherein the first illumination system further comprises:
a handle piece comprising a rigid light guide, the rigid light guide being configured for piercing parts of the human body neighboring at least one of the visceral cavity, hollow organ or vitreous body;
a first radiation source incorporated into the handle piece, wherein the rigid light guide is optically connected to the radiation source; and
a second radiation source incorporated into the handle piece, wherein the rigid light guide is optically connected to the radiation source;
wherein, in the first operating state, only the first radiation source is in operation, and in the second operating state, only the second radiation source is in operation,
wherein the first radiation source emits radiation with a spectrum having a bandwidth of at least 200 nm, and in particular emits radiation with a spectrum having a bandwidth of at least 250 nm, the radiation emitted by the first radiation source being in a range from 380 nm to 780 nm; and
wherein the second radiation source emits only radiation with a spectrum that is free from the pass band of the observation filter, and that comprises in particular a bandwidth of not more than 150 nm;
the ophthalmology microscopy system further comprising:
a second illumination system providing a second illumination beam path intersecting the focal plane of the imaging system at a constant angle of more than 80°, the second illumination system being located in the same housing as the imaging system; and
further comprising a controller connected to the imaging system and the first illumination system and adapted to optionally switch the imaging system and the first illumination system simultaneously either into the first or the second operating state.

* * * * *